United States Patent [19]

Shetty et al.

[11] Patent Number: 4,719,106

[45] Date of Patent: * Jan. 12, 1988

[54] IODOPHOR COMPOSITION WITH IMMEDIATE AND LONG ACTION MICROBICIDAL ACTION

[75] Inventors: Bola V. Shetty, Stamford, Conn.; Peter Hofer, Liestal, Switzerland

[73] Assignee: Euroceltique S.A., Luxembourg, Luxembourg

[*] Notice: The portion of the term of this patent subsequent to Mar. 18, 2003 has been disclaimed.

[21] Appl. No.: 850,522

[22] Filed: Apr. 11, 1986

[51] Int. Cl.⁴ .................. A61K 31/79; A61K 33/18
[52] U.S. Cl. ............................... 424/80; 424/150
[58] Field of Search ............................ 424/80, 150

[56] References Cited

U.S. PATENT DOCUMENTS 4,576,818  3/1986  Shetty .................. 424/150

Primary Examiner—Leonard Schenkman
Attorney, Agent, or Firm—Steinberg & Raskin

[57] ABSTRACT

New iodophor compositions are provided which are mixtures of polydextrose-iodine and polyvinylpyrrolidone-iodine. Such mixtures containing polydextrose-iodine and polyvinylpyrrolidone-iodine, wherein the ratio by weight of polydextrose to polyvinylpyrrolidone is between 20–80: 80–20, have an immediate bactericidal activity upon application and also a long lasting microbicidal activity. The immediate microbicidal acitivity is faster and more effective than by the use of either the polydextrose-iodine alone or the polyvinylpyrrolidone-iodine alone, and the effect is more long lasting than in the case of the use of either polydextrose-iodine alone or polyvinylpyrrolidone-iodine alone.

8 Claims, No Drawings

IODOPHOR COMPOSITION WITH IMMEDIATE AND LONG ACTION MICROBICIDAL ACTION

BACKGROUND OF THE INVENTION

Iodphors are water-soluble physiologically-acceptable complexes of iodine with organic carriers. The general class of organic iodophors comprises two distinct polymer groups, namely the non-detergent, nonionic and non-surface active polymers, and the detergent-/surface-active polymers which includes both nonionic, anionic and cationic surface-active polymers.

The most commonly used organic iodophor is polyvinylpyrrolidone-iodine. This is also known as povidone-iodine, and will be referred to as such hereafter.

Povidone-iodine and its preparation has been described in U.S. Pat. No. 2,739,922. For many years, this was substantially the only non-detergent, nonionic iodophor which has been found to be suitable for germicidal action in man and animals, as well as in environmental uses.

U.S. patent application Ser. No. 638,558, filed Aug. 7, 1984 describes a new nonionic, non-surface active iodopor which is a complex of iodine with polydextrose and which is herein referred to as polydextrose-iodine.

Polydextrose, which is described in U.S. Pat. Nos. 3,766,105 and 3,786,794, is a white to tan powder occurring in both water soluble and water insoluble forms and having an average molecular weight of about 1,500 to 36,000, with the water soluble polydextrose having an average molecular weight of about 2,500 to 18,000, and water insoluble polydextrose having an average molecular weight of between 6,000 to 36,000.

The average molecular weight of commercially available polydextrose is 1,500, ranging from 162 to approximately 20,000. This molecular weight range ensures a high degree of water solubility and relatively low viscosity. The molecular weight range for commercially available polydextrose is:

| MOLECULAR WEIGHT RANGE | PERCENT |
| --- | --- |
| 162–5,000 | 88.7 |
| 5,000–10,000 | 10.0 |
| 10,000–16,000 | 1.2 |
| 16,000–18,000 | 0.1 |

The polydextrose-iodine complexes of U.S. patent application Ser. No. 638,588 contain up to 20% by weight of iodine, generally between 1–20%, preferably 2–16% and most preferably 2–10%.

Both the povidone-iodine and the polydextrose-iodine complexes have good microbicidal activity and can be used for humans, animals and environmental treatment compositions. However, improvements in these iodophors has been sought, particularly from the standpoint of speed of action, that is speed of first kill, and duration of action, that is long-lasting kill.

SUMMARY OF THE INVENTION

It is accordingly a primary object of the present invention to provide iodophor compositions having improved microbicidal activity.

It is another object of the present invention to provide iodophor compositions which have both a more immediate microbicidal action and a more long lasting microbicidal action.

Other objects and advantages of the present invention will be apparent from a further reading of the specification and of the appended claims.

With the above and other objects in view, the present invention mainly comprises iodophor compositions comprising a mixture of polydextrose-iodine and povidone-iodine in a ratio by weight of 20–80% polydextrose to 80–20% povidone.

Preferably, the mixture of polydextrose-iodine and povidone-iodine contains 30–70% by weight polydextrose to 70–30% by weight povidone, and most preferably 50–50% by weight of each.

Any of the known povidone-iodine complexes can be used for the purposes of the present invention and any of the polydextrose-iodine complexes of application Ser. No. 638,558 can be used for the purposes of the present invention.

While the invention is not meant to be limited to any theory as to how or why the iodophor mixtures of the present invention provide more immediate and more long lasting action than either polydextrose-iodine alone or povidone-iodine alone, the following theory is given hopes of leading to further research in this field.

It is believed that polydextrose-iodine provides a rapid but short acting microbicidal action and that povidone-iodine provides a slower but more long lasting action than does polydextrose-iodine. However, the microbicidal action, measured by kill effect, of povidone-iodine, although long lasting, is not fully effective because the time lag for povidone-iodine to take effect is such that there is a bacteria build-up to a level such that the povidone-iodine is not sufficiently effective to achieve complete kill. It is believed that the polydextrose-iodine provides an immediate kill and maintains the level of kill to a sufficient extent so that when the povidone-iodine takes effect, there is a complete and long lasting kill effect.

In any event, the kill effect is more immediate when using a mixture of polydextrose-iodine and povidone-iodine according to the present invention, than if the polydextrose-iodine is used alone. While this is not fully understood, it is belived that there is some synergistic action between the povidone-iodine and the polydextrose-iodine to provide the more immediate action. Likewise, it is not understood why the kill effect is more long lasting with the mixture of povidone-iodine and polydextrose-iodine according to the invention than in the case of the use of povidone iodine alone. Apparently, there is some sort of synergistic action with respect to long lasting effect also.

A further advantage of the present invention is that the amount of iodine required to form a stable form of the iodophor composition of the present invention is the same or less than that required in the case of povidone-iodine alone and considerably less than that required in the case of polydextrose-iodine alone.

The iodophor compositions of the present invention may be prepared and used in dry form as a powder or in solution form. The amount of available (titratable) iodine present in the mixed iodophor compositions of the invention depends on the form chosen for the composition, the ratio of polydextrose to povidone, and the purpose for which the composition is to be used, e.g. for treating humans, or for environmental purposes such as the cleaning of hospitals and the like. Preferably, the compositions of the invention will contain up to 20% of iodine, preferably 2–15%, and in the case of human treatment, preferably 0.02–2.0%. All percents are by weight.

The iodophor compositions of the present invention can be stabilized in the same manner as simple iodophor compositions by the addition of an oxidizing agent, particularly an alkali metal iodate. Such oxidizing agents are used in concentrations of about 0.001–0.75%, preferably 0.05–0.5%.

Also, as in the case of simple iodophor compositions the pH of antiseptic solutions thereof can be adjusted by buffering, particularly in the case of treatment of humans or animals, to between 4.0–7.5, preferably 4.5–6.5, and most preferably 5.0–6.0. In the case of the use of the compositions of the treatment of non-living objects such as hospital corridors, the pH of the solutions may be lowered to the strong-moderate acid range.

The compositions of the present invention may be prepared most simply by adding iodine to a mixture of polydextrose and povidone. The iodine may be added as solid iodine or as a solution of iodine and iodide.

DESCRIPTION OF THE PREFERRED EMBODIMENTS

The following examples are given to further illustrate the present invention. The scope of the invention is not, however, meant to be limited to the specific details of the examples.

In these examples, the polydextrose which is used is the commercial polydextrose of the type described above and the povidone (in the examples referred to as "PVP") is also of the common commercially available type.

EXAMPLE 1

INGREDIENT 10.0 gm polydextrose
10.0 gm PVP-V-30
6.8 cc of $KI_3$ solution (585.0 mg $I_2$/cc)
40.0 cc water.

PROCEDURE

Ten grams of polydextrose and 10.0 gm of PVP were dissolved in 40 cc of water and the pH adjusted to 3.6 with dilute sodium hydroxide solution. With stirring 6.8 cc iodine solution (prepared by reacting 82.0 gm KI, 145.0 gm $I_2$ and 200 cc water) were added and heated to 55° C. for one hour. The resulting solution was filtered and freeze-dried.

% Av. $I_2$ in the powder=15.74.

EXAMPLE 2

INGREDIENT 5.0 gm polydextrose
15.0 gm PVP-K30
6.8 cc iodine solution (prepared same was in Example 1)
40.0 cc water.

PROCEDURE

Polydextrose and PVP were placed in a round bottomed three-necked flask provided with a stirrer, condenser and a thermometer. With stirring it was dissolved in water and the pH was adjusted to 3.6. Then iodine solution was added and the mixture was heated to 55° with stirring for one hour. The resulting solution was cooled to RT, filtered and freeze dried.

% Av. $I_2$ in the freeze-dried powder=15.23.

EXAMPLE 3

INGREDIENT 15.0 gm polydextrose
5.0 gm PVP-K30
6.8 cc iodine solution
40.0 cc water.

PROCEDURE

Polydextrose and PVP were dissolved in water with stirring and the pH adjusted to 3.6. With stirring iodine solution was added, heated to 55° C. for one hour, cooled to RT and freeze dried.

% Av. $I_2$ in the powder=14.17.

EXAMPLE 4

INGREDIENT 11.0 gm polydextrose
9.0 gm PVP-K30
4.10 cc iodine solution
40.0 cc water.

PROCEDURE

Polydextrose and PVP were dissolved in water and the pH was adjusted to 3.6. With stirring, iodine solution was added, heated to 55° C. for one hour, cooled and freeze dried to get powder.

% Av. $I_2$=9.71.

EXAMPLE 5

INGREDIENT 10.0 gm polydextrose
10.0 gm PVP-K30
4.10 cc of iodine solution
40.0 cc water.

PROCEDURE

Polydextrose and PVP were dissolved in water and the pH was adjusted to 3.6 if required. With stirring, iodine solution was added, heated to 55° C. for one hour, cooled to RT and freeze-dried.

% Av. $I_2$=9.01.

EXAMPLE 6

INGREDIENT 9.0 gm polydextrose
11.0 gm PVP-K30
4.10 cc iodine solution
40.0 cc water.

PROCEDURE

Polydextrose and PVP were dissolved in water and the pH adjusted to 3.6. With stirring, iodine solution was added, heated to 55° C. for one hour, cooled to RT and freeze-dried.

% Av. $I_2$=9.14.

EXAMPLE 7

INGREDIENT 10.0 gm polydextrose
10.0 gm PVP-K30
4.10 cc of iodine solution
40.0 cc water.

PROCEDURE

Polydextrose and PVP were dissolved in water and the solution heated to 60° C. for two hours, cooled to RT and then iodine solution was added with stirring. It was heated again, with stirring to 55° C. for one hour, cooled to RT and freeze-dried.

% Av. $I_2$ = 10.41.

EXAMPLE 8

INGREDIENT 15.0 gm polydextrose
5.0 gm PVP-K30
4.0 gm elemental iodine
40.0 cc water.

PROCEDURE

Polydextrose and PVP were dissolved in water and the pH adjusted to 3.6. With stirring, iodine was added portionwise, heated to 55° C. for one hour, cooled to RT and freeze-dried.

% Av. $I_2$ = 6.78.

EXAMPLE 9

INGREDIENT 5.0 gm polydextrose
15.0 gm PVP-K30
4.0 gm elemental iodine
40.0 cc water.

PROCEDURE

Polydextrose and PVP were dissolved in water and the pH adjusted to 3.6. With stirring, iodine was added, heated to 55° C. for one hour, cooled to RT and freeze-dried.

% Av. $I_2$ = 8.24.

EXAMPLE 10

INGREDIENT 10.0 gm polydextrose
10.0 gm PVP-K30
4.0 gm elemental iodine
40.0 cc water.

PROCEDURE

Polydextrose and PVP were dissolved in water. With stirring, iodine was added portionwise, heated to 55° C. for one hour, and cooled to RT and freeze-dried.

% Av. $I_2$ (liquid) = 4.85 w/w.
% Av. $I_2$ (freeze-dried powder) = 13.33.
% iodide = 3.27.

EXAMPLE 11

INGREDIENT 10.0 gm polydextrose
10.0 gm PVP-K30
3.6 gm elemental iodine
70.0 cc water.

PROCEDURE

Polydextrose and PVP were dissolved in water with stirring, iodine was added, heated to 55° C. for one hour, and cooled to RT.

% Av. $I_2$ (liquid) = 2.60.
% Av. $I_2$ (freeze-dried powder) = 11.75.
% iodine (powder) = 1.96.

EXAMPLE 12

INGREDIENT 10.0 gm polydextrose
10.0 gm PVP-K30
4.0 gm elemental iodine
70.0 cc water.

PROCEDURE

With stirring, polydextrose and PVP were dissolved in water, iodine was added portionwise, heated to 55° C. for one hour, cooled to RT and freeze-dried.

% Av. $I_2$(powder) = 11.61.
% iodine = 2.68.

EXAMPLE 13

INGREDIENT 10.0 gm polydextrose
10.0 gm PVP-K30
4.0 gm elemental iodine
70.0 cc water.

PROCEDURE

With stirring, polydextrose and PVP were dissolved in water, iodine was added portionwise, heated to 55° C. for one hour, cooled to RT and freeze-dried.

% Av. $I_2$ (powder) = 11.61.
% iodine = 2.68.

EXAMPLE 14

INGREDIENT 60.0 gm polydextrose
60.0 gm PVP-K30
24.0 gm elemental iodine
0.86 gm potassium iodide
420.0 cc water.

PROCEDURE

With stirring, polydextrose and PVP were dissolved in 400 cc of water. Potassium iodide dissolved in 20 cc of water was added to the solution. To the clear solution, iodine was added, heated to 55° C. for one hour, and cooled to RT.

% Av. $I_2$ (liquid) = 3.45.
% Av. $I_2$ (freeze-dried powder) = 13.21.

EXAMPLE 15

INGREDIENT 250.0 gm polydextrose
250.0 gm PVP-K30
91.0 gm elemental iodine
3.58 gm potassium iodide
1750.0 cc water.

PROCEDURE

With stirring, polydextrose and PVP were dissolved in 1500 cc of water and potassium iodide dissolved in 250 cc of water was added to it. To the clear solution, iodine was added, heated to 55° C. for one hour, and cooled to RT.

% Av. $I_2$ (liquid) = 3.49 w/w.
% Av. $I_2$ (freeze-dried powder) = 12.02 w/w.
% Iodide (powder) = 0.93 w/w.

EXAMPLE 16

INGREDIENT 12.0 gm polydextrose
8.0 gm PVP-K30
2.91 gm elemental iodine
0.11 gm potassium iodide
55.0 cc water.

PROCEDURE (a) Two hundred mililiter solution of 5% w/w polydextrose was charged to a 200 ml capacity ultra filtration cell with Amicon YM 2 membrane. Under 50 psi of nitrogen the solution was concentrated to approximately 10%. The solution was re-diluted with distilled water to 200 ml and concentrated. The procedure was repeated, the solid in the membrane was collected and freeze-dried.

Weight of the freeze-dried powder was 8.6 gm and it had mol. wt. greater than 1000.

(b) Eight grams of PVP and 8.0 gm of fractionated polydextrose (M:W>1000) were dissolved in 50 cc of water and 0.11 gm of KI dissolved in 6 cc of water was added to it. To the clear solution, 2.91 gm of iodine was added with stirring, heated to 55° C. for one hour, cooled to RT and freeze-dried % Av. $I_2$ (freeze-dried powder)=10.02.
% Iodide=0.71.

EXAMPLE 17

INGREDIENT 8.0 gm polydextrose (M.W.>1000)
8.0 gm PVP-K30
2.91 gm elemental iodine
0.11 gm potassium iodide
56.0 cc water.

PROCEDURE

With stirring polydextrose (M.W.>1000 obtained by procedure given in Example 16) and PVP were dissolved in 50 cc of water and 0.11 gm KI dissolved in 6 cc of water was added to it. To the clear solution, iodine was added with stirring, heated to 55° C. for one hour and freeze-dried.

% Av. $I_2$ (freeze-dried powder)=10.19.
% Iodide=0.71.

EXAMPLE 18

INGREDIENT 8.0 gm polydextrose
8.0 gm PVP-K30
2.91 gm elemental iodine
0.77 gm potassium iodide
56.0 cc water.

PROCEDURE

With stirring polydextrose and PVP were dissolved in 50 cc of water and KI dissolved in 6 cc of water was added to it. To the clear resulting solution, iodine was added with stirring, heated to 55° C. for one hour and cooled to RT. It was filtered through a GF/D glass fiber filter.

% Av. $I_2$ (liquid)=2.98.
% Av. $I_2$ (freeze-dried powder)=11.29.
% Iodide (powder)=4.58.

EXAMPLE 19

INGREDIENT 8.0 gm polydextrose (M.W.>1000)
8.0 gm PVP-K30
2.91 gm elemental iodine
0.91 gm potassium iodide
56.0 cc water.

PROCEDURE

With stirring polydextrose and PVP were dissolved in 50 cc of water and KI dissolved in 6 cc of water was added to it. To the clear solution, iodine was added with rapid stirring, heated to 55° C. for one hour, cooled to RT, and filtered through a GF/D glass fiber filter.

% Av. $I_2$ (liquid)=3.82.
% Iodide (liquid)=0.89.
% Av. $I_2$ (freeze-dried powder)=13.07.
% Iodide (powder)=4.05.

EXAMPLE 20

INGREDIENT 12.0 gm polydextrose
12.0 gm PVP-K30
4.37 gm iodine
0.38 gm KI
100.0 cc water.

PROCEDURE

With stirring polydextrose and PVP were dissolved in 80 cc of water and KI dissolved in 20 cc of water was added to it. To the clear solution, iodine was added with rapid stirring, heated to 55° C. for one hour, cooled to RT, and filtered through a GF/D glass fiber filter.

% Av. $I_2$ (liquid)=2.76
% Av. $I_2$ (freeze-dried powder)=11.42
% Iodide (powder)=1.11.

EXAMPLE 21

INGREDIENT 12.0 gm polydextrose (M.W.>1000)
12.0 gm PVP-K30
4.19 gm iodine
1.89 gm KI
100.0 cc water.

PROCEDURE

With stirring polydextrose and PVP were dissolved in 80 cc of water and KI dissolved in 20 cc of water was added to it. To the clear solution, iodine was added with rapid stirring, heated to 55° C. for one hour, cooled to RT, and filtered through a GF/D glass fiber filter.

% Av. $I_2$ (liquid)=2.82.
% Av. $I_2$ (liquid)=1.20.
% Av. $I_2$ (freeze-dried powder)=12.31.
% Iodide (powder)=1.81.

EXAMPLE 22

INGREDIENT 12.0 gm polydextrose
12.0 gm PVP-K30
4.19 gm iodine
1.89 gm KI
100.0 cc water

PROCEDURE

With stirring polydextrose and PVP were dissolved in 80 cc of water and KI dissolved in 20 cc of water was added to it. To the clear solution, iodine was added with rapid stirring, heated to 55° C. for one hour, cooled to RT, and filtered through a GF/D glass fiber filter.

% Av. I$_2$ (liquid)=2.73.
% Iodide (liquid)=1.02.
% Av. I$_2$ (freeze-dried powder)=12.71.
% Iodide (powder)=5.04.

EXAMPLE 23

INGREDIENT 12.0 gm polydextrose
12.0 gm PVP-K30
3.87 gm iodine
1.85 gm KI
100.0 cc water.

PROCEDURE

With stirring polydextrose and PVP were dissolved in 80 cc of water and KI dissolved in 20 cc of water was added to it. To the clear solution, iodine was added with rapid stirring, heated to 55° C. for one hour, cooled to RT, and filtered through a GF/D glass fiber filter.

% Av. I$_2$ (liquid)=2.51.
% Iodine (liquid)=0.83.
% Av. I$_2$ (freeze-dried powder)=11.54.
% Iodine (powder)=5.17.

EXAMPLE 24

INGREDIENT 12.0 gm polydextrose
12.0 gm PVP-K30
1.62 gm iodine
3.61 gm KI
100.0 cc water.

PROCEDURE

With stirring polydextrose and PVP were dissolved in 80 cc of water and KI dissolved in 20 cc of water was added to it. To the clear solution, iodine was added with rapid stirring, heated to 55° C. for one hour, cooled to RT, and filtered through a GF/D glass fiber filter.

% Av. I$_2$ (liquid)=2.41.
% Iodine (liquid)=0.89.
% Av. I$_2$ (freeze-dried powder)=11.04.
% Iodide (powder)=4.07.

EXAMPLE 25

INGREDIENT 12.0 gm polydextrose
12.0 gm PVP-K30
3.61 gm iodine
1.86 gm KI
100.0 cc water.

PROCEDURE

With stirring polydextrose and PVP were dissolved in 80 cc of water and KI dissolved in 20 cc of water was added to it. To the clear solution, iodine was added with rapid stirring, heated to 55° C. for one hour, cooled to RT, and filtered through a GF/D glass fiber filter.

% Av. I$_2$ (liquid)=2.41.
% Iodide (liquid)=0.87.
% Av. I$_2$ (freeze-dried powder)=11.04.
% Iodide (powder)=5.65.

EXAMPLE 26

INGREDIENT 12.0 gm polydextrose
12.0 gm PVP-K30
3.68 gm iodine
1.77 gm KI
100.0 cc water.

PROCEDURE

With stirring, polydextrose and PVP were dissolved in 80 cc of water and potassium iodide dissolved in 20 cc of water was added to it. To the clear solution, iodine was added with rapid stirring, heated to 55° C. for one hour, cooled to RT, and filtered through a GF/D glass fiber filter.

% Av. I$_2$ (liquid)=2.70.
% Iodide (liquid)=1.40.
% Av. I$_2$ (freeze-dried powder)=9.26.
% Iodide (powder)=6.80.

EXAMPLE 27

INGREDIENT 50.0 gm polydextrose
50.0 gm PVP
14.7 gm iodine
5.96 gm KI
417.0 cc water.

PROCEDURE

With stirring, polydextrose and PVP were dissolved in 344 cc of water and potassium iodide dissolved in 84 cc of water was added to it. To the clear solution, iodine was added with rapid stirring, heated to 55° C. for one hour, cooled to RT, and filtered through a GF/D glass fiber filter.

% Av. I$_2$ (liquid)=2.50.
% Iodide (liquid)=0.94.

EXAMPLE 28

INGREDIENT 50.0 gm polydextrose
50.0 gm PVP
14.42 gm iodine
5.80 gm KI
417.0 cc water.

PROCEDURE

With stirring, polydextrose and PVP were dissolved in 333 cc of water and potassium iodide dissolved in 84 cc of water was added to it. To the clear solution, iodine was added with rapid stirring, heated to 55° C. for one hour, cooled to RT, and filtered through a GF/D glass fiber filter.

% Av. I$_2$ (liquid)=2.37.
% Iodide (liquid)=0.81.
% Av. I$_2$ (freeze-dried powder)=11.02.
% Iodide (powder)=5.69.

EXAMPLE 29

INGREDIENT 50.0 gm polydextrose
50.0 gm PVP-K30
14.42 gm iodine 5.54 gm KI
438.0 cc water.

PROCEDURE

With stirring, polydextrose and PVP were dissolved in 350 cc of water and potassium iodine dissolved in 88 cc of water was added to it. To the clear solution, iodine was added with rapid stirring, heated to 55° C. for one hour, cooled to RT, and filtered through a GF/D glass fiber filter.

% Av. $I_2$ (freeze-dried powder) = 11.24.

EXAMPLE 30

INGREDIENT 50.0 gm polydextrose
50.0 gm PVP-K30
14.42 gm iodine
5.28 gm KI
438.0 cc water.

PROCEDURE

With stirring, polydextrose and PVP were dissolved in 350 cc of water and potassium iodine dissolved in 88 cc of water was added to it. To the clear solution, iodine was added with rapid stirring, heated to 55° C. for one hour, cooled to RT, and filtered through a GF/D glass fiber filter.

% Av. $I_2$ (freeze-dried powder) = 10.53.

EXAMPLE 31

INGREDIENT 50.0 gm polydextrose
50.0 gm PVP-K30
14.42 gm iodine
5.60 gm KI
438.0 cc water.

PROCEDURE

With stirring, polydextrose and PVP were dissolved in 438 cc of water and iodine was added to it. With rapid stirring potassium iodine was added to the solution. It was heated to 55° C. for one hour, cooled to RT, filtered through a GF/D glass fiber filter and freeze-dried.

% Av. $I_2$ (freeze-dried powder) = 10.11.

EXAMPLE 32

INGREDIENT 50.0 gm polydextrose
50.0 gm PVP-K30
14.42 gm iodine
5.70 gm KI
438.0 cc water.

PROCEDURE

Polydextrose and PVP were dissolved in 438 cc of water and with a rapid stirring, iodine followed by potassium iodide were added to the solution. It was heated to 55° C. for one hour, cooled to RT, filtered through a GF/D glass fiber filter and freeze-dried.

% Av. $I_2$ (freeze-dried powder) = 10.93.

EXAMPLE 33

INGREDIENT 50.0 gm polydextrose
50.0 gm PVP-K30
14.42 gm iodine
5.65 gm KI
438.0 cc water.

PROCEDURE

With rapid stirring, polydextrose and PVP were dissolved in 438 cc of water, and then iodine followed by potassium iodine were added to the solution. It was heated to 55° C. for one hour, cooled to RT and filtered through a GF/D glass fiber filter.

% Av. $I_2$ (liquid = 2.69.
% Av. $I_2$ (freeze-dried powder) = 10.20.

EXAMPLE 34

INGREDIENT 80.0 gm polydextrose
80.0 gm PVP-K30
32.0 gm iodine
2.16 gm KI
560.0 cc water.

PROCEDURE

Polydextrose and PVP were dissolved in water. To the clear solution, potassium iodine followed by iodine were added with rapid stirring. The solution was stirred for 0.5 hr. at RT and then it was heated with stirring at 55° C. for one hour. Cooled to RT and freeze dried.

wt of the freeze-dried powder = 168.9.
% Av. $I_2$ = 8.54.

What is claimed is:

1. Iodophor composition with immediate and long lasting microbicidal action, comprising povidone-iodine and polydextrose-iodine wherein the ratio by weight of povidone to polydextrose is about 20–80:80–20.

2. Iodophor composition according to claim 1 wherein the ratio of povidone to polydextrose is about 30–70:70–30.

3. Iodophor composition according to claim 1 wherein the ratio of povidone to polydextrose is about 50:50.

4. Iodophor composition according to claim 1 wherein the ratio of povidone to polydextrose is about 80:20.

5. Iodophor composition according to claim 1 wherein the ratio of povidone to polydextrose is about 20:80.

6. Iodophor composition according to claim 1 wherein the ratio of povidone to polydextrose is about 30:70.

7. Iodophor composition according to claim 1 wherein the ratio of povidone to polydextrose is about 70:30.

8. The iodophor composition of claim 1, containing up to 20% of available iodine.

* * * * *